United States Patent [19]

Soderlund et al.

[11] Patent Number: 4,938,821
[45] Date of Patent: Jul. 3, 1990

[54] METHOD AND APPARATUS FOR MANUFACTURE OF A DIAPER WITH ELASTIC MARGINS

[75] Inventors: J. Donald Soderlund, Bellevue; Richard H. Young, Puyallup; E. Peter Lancaster, Gig Harbor, all of Wash.

[73] Assignee: Weyerhaeuser Company, Tacoma, Wash.

[21] Appl. No.: 89,197

[22] Filed: Aug. 24, 1987

Related U.S. Application Data

[62] Division of Ser. No. 850,183, Apr. 10, 1986.

[51] Int. Cl.$^5$ .................. B32B 31/08; B32B 31/18
[52] U.S. Cl. .................... 156/85; 156/163; 156/164; 156/251; 156/269; 156/301; 156/324; 156/495; 156/522; 156/530; 156/552; 156/553; 156/544; 264/230
[58] Field of Search ............... 156/85, 163, 164, 251, 156/269, 301, 324, 495, 522, 530, 552, 553, 544; 264/230, 229; 2/400; 604/385.1

[56] References Cited

U.S. PATENT DOCUMENTS

| | | | |
|---|---|---|---|
| 2,125,495 | 8/1938 | French | 156/163 |
| 2,502,772 | 4/1950 | Winstead | 156/163 |
| 2,905,581 | 9/1959 | Maxey | 156/163 |
| 2,976,199 | 3/1961 | Rand | 156/553 |
| 3,245,407 | 4/1966 | Mason | 2/407 |
| 3,819,401 | 6/1974 | Massengale et al. | 156/85 |
| 3,912,565 | 10/1975 | Koch et al. | 264/230 |
| 4,014,724 | 3/1977 | Rausing | 264/230 |
| 4,048,281 | 9/1977 | Brunmett et al. | 264/230 |
| 4,081,301 | 3/1978 | Buell | 156/269 |
| 4,261,782 | 5/1981 | Teed | 156/522 |
| 4,300,967 | 11/1981 | Sigl | 156/301 |
| 4,335,070 | 6/1982 | Yazawa et al. | 264/230 |
| 4,409,049 | 10/1983 | Passafiume et al. | 156/301 |
| 4,432,823 | 2/1984 | Moore | 156/495 |
| 4,450,026 | 5/1984 | Pieniak et al. | 156/301 |
| 4,464,217 | 8/1984 | Dickover et al. | 156/164 |
| 4,507,163 | 3/1985 | Menard | 156/269 |
| 4,525,229 | 6/1985 | Suzuki et al. | 156/301 |
| 4,543,154 | 9/1985 | Reiter | 156/85 |
| 4,566,923 | 1/1986 | Mueller | 264/230 |
| 4,582,550 | 4/1986 | Sigl | 604/385.1 |
| 4,626,305 | 12/1986 | Suzuki et al. | 156/164 |
| 4,642,151 | 2/1987 | Coenen | 156/552 |
| 4,663,106 | 5/1987 | Pomplum et al. | 156/85 |
| 4,675,068 | 6/1987 | Lundmark | 156/495 |

Primary Examiner—Jerome Massie

[57] ABSTRACT

The present invention is a method and apparatus for making a diaper having one or more elastic margins. The diaper uses for the entire moisture permeable backing sheet an elastomeric material of the type that is heat unstable and relatively inelastic in its unshrunk form and stable and relatively elastic in its heat shrunk form. Diapers made using one of these materials as a backing sheet can be conventionally assembled. After assembly, the marginal areas, which may be either or both of the transverse and longitudinal margins, may be heated to a sufficient temperature for shrinkage to occur in the backing sheet. This shrinkage will only occur when the backing sheet is unrestrained. The method provides for the maintenance of longitudinal tension in the central portion of an end-to-end assembly of diaper units while relaxing the edge tension on the units. This is accomplished in the present diaper making machine by passing the assembly over a series of rollers which are of cylindrical form in the central portion and are tapered at each end. The marginal portions overhang the tapered portion where they are free to shrink after heating. If an elastic waist construction is desired, the diapers are similarly heated in a transverse direction whereupon any transverse tension is relaxed to enable transverse shrinkage to occur. While the preferred diaper uses the heat shrinkable material as the entire backing film, it is within the scope of the invention to insert ribbons of this material along the appropriate marginal edges of the diapers and use conventional backing film materials.

16 Claims, 7 Drawing Sheets

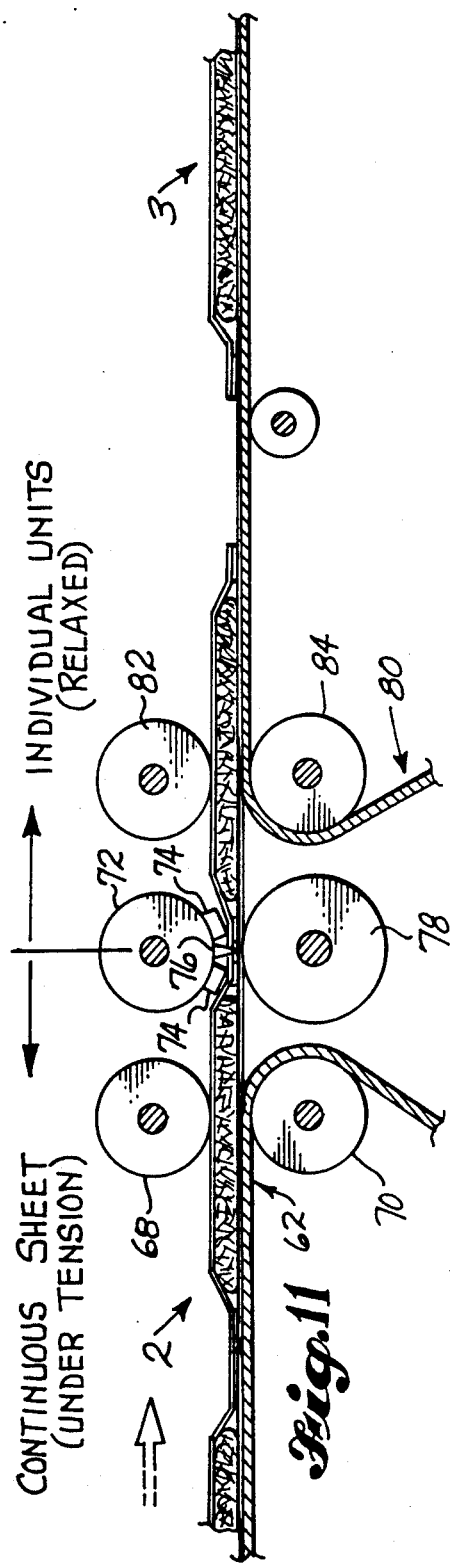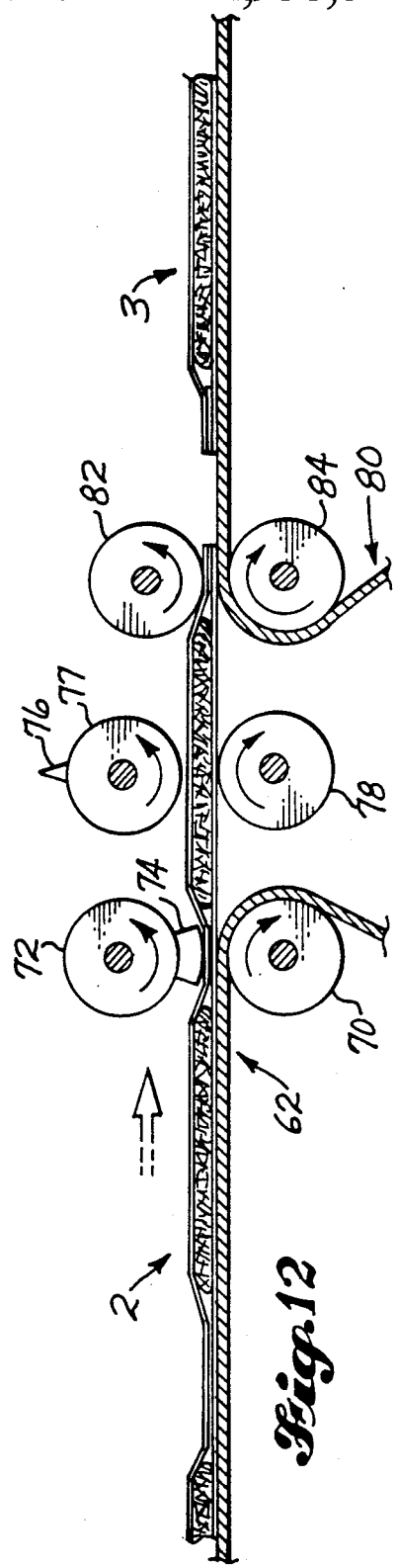

METHOD AND APPARATUS FOR MANUFACTURE OF A DIAPER WITH ELASTIC MARGINS

This application is a division, of application Ser. No. 850,183, filed 4/10/86.

BACKGROUND OF THE INVENTION

The present invention comprises a disposable diaper having elasticized leg and/or waist encircling areas, and a method and apparatus for manufacture of the diapers. The elastic areas are provided by a heat shrinkable elastomeric material of the type that is heat unstable and relatively inelastic in its unshrunk form and stable and relatively elastic in its heat shrunk form.

Garments having localized elasticized areas for ensuring relatively tight fits around such body zones as wrists, waist or thighs have long been manufactured. Initially, and still to a certain extent, the elastic has been applied by sewing while held in a stretched condition. When relaxed, the elastic causes a shirring or puckering of the elasticized area of the garment. Sewing elastic is a relatively slow and expensive manufacturing operation. Many inventors have dedicated their energy to finding simpler methods of attaching elastic. As one example, Gray, U.S. Pat. No. 1,544,312, used a partially cured rubber strip which was mechanically crimped to the garment and later heat cured. Maxey, U.S. Pat. No. 2,905,181, used a band of nitrile rubber which was heat sealed to a moisture impervious polyvinyl chloride film.

Disposable diapers for infants have been the subject of a great deal of inventive activity to prevent leakage. One very successful effort in this regard was the use of a box pleat around the thigh areas of an infant. A diaper of this type is described by Duncan et al in U.S. Pat. Reissue No. 26,152. While this construction represented a major step forward, it still did not provide an entirely satisfactory solution to the problem of leakage. Another move toward an ultimate solution is described by Buell in U.S. Pat. No. 3,860,003. The Buell diaper used narrow ribbons of stretched elastic along each longitudinal side margin in the thigh encircling areas. This construction has been so highly successful that it has been emulated and improved upon by subsequent inventors in the field. The following U.S. Pat. Nos. are exemplary of these later developments: Woon et al, 4,050,462; Strickland et al, 4,253,461; Sigl et al, 4,437,860; and Teed, 4,405,397. The Strickland et al product represents a move beyond diapers suitable only for infants and is a product principally adapted for use by incontinent adults. Schaar, in U.S. Pat. No. 3,951,150, shows an infant diaper having an elasticized waist encircling area designed for reducing leakage from that portion of the product.

The above list is presented primarily to indicate historical development of diapers having elasticized zones and is not intended to be fully inclusive of all such products which have been developed. All of these examples use an elastic material which is normally a relatively narrow ribbon of natural rubber adhesively bonded between the backsheet and cover sheet of the diaper. The use of adhesive bonding, usually with flexible hot melt adhesives, has enabled the production of elasticized disposable diapers at high rates of speed.

During the later part of the time period represented by the above patents, a parallel approach has been developing using non-rubber elastomeric materials. These are based on a wide variety of synthetic polymers which typically are uniaxially or biaxially stretched during their manufacture into relatively thin film. This stretching induces stresses which are frozen into the product when it is cooled while being held under uniaxially or biaxially applied tension. Certain of these materials retain a memory of their dimensions in the original unstretched state. Depending on the particular polymer chosen, and its method of manufacture, by heating to a specific predetermined temperature, the material will shrink back to approximately this original dimension. These polymeric products can be readily tailored to be of elastomeric nature. The term "elastomeric" is interpreted in various ways, but here it is generally meant to mean that a product may be stretched to at least about 120-140% of its original length and return to that length without permanent deformation when the stretching force is released. Many of the products available are relatively inelastic in their uni- or biaxially oriented heat unstable forms and would not meet the above criterion. However, these become fully elastic when heat shrunk. A further feature of many of these polymers is that they can be heat sealed or bonded to other materials at a temperature below the point which will cause heat shrinkage. This is especially convenient for the manufacture of elasticized garments since it infers that the material may be applied without the need to be held under tension. A subsequent heating step is all that is needed to produce an elasticized zone.

While many polymeric materials of generically different types can be cited as being useful in the above application, the following U.S. Pat. Nos. should be considered as being exemplary: Perrin et al, 2,200,249; White, 2,953,551; Cook et al, 3,086,242; Holden et al, 3,265,765; and Pellicciari et al, 3,551,540. The following British patents Nos. also disclose useful polymer compositions: 866,819; 866,820; 866,821; 866,822; and 1,010,064.

The original application of heat shrunk elastic to garments appears to have been done by Mason as shown in U.S. Pat. No. 3,245,407. Here the inventor produced plastic panties with heat shrunk elasticized leg and waist zones. Mason showed other applications as well. Later, Althouse in U.S. Pat. No. 3,639,917 showed the use of heat shrinkable elastic ribbons in other applications such as wrist cuffs on disposable hospital garments. Massengale et al, in U.S. Pat. No. 3,819,401, and Koch et al, in U.S. Pat. No. 3,912,565 show the use of specific heat shrinkable materials for making elasticized areas in garments such as panties. Schirmer, in U.S. Pat. No. 3,755,062, shows the use of a film of heat shrinkable materials for making bulked fabric articles such as nonwoven rugs.

Natural rubber is a relatively expensive product and for this and other reasons, it is normally used in the form of threads or relatively narrow ribbons when used to elasticize portions of garments. A disadvantage of this construction is that the elasticized portion of the garment frequently presents a small and very narrow bearing area against the skin of the wearer. Thus, if the purpose of the elasticized area is to prevent leakage, as in the case of an elastic leg diaper, the elastic must be held under relative high tension to provide a tight seal. This will frequently result in chafing and general discomfort to the wearer. One solution to this problem has been to use parallel narrow strips of rubber elastic to increase the bearing area. A diaper having this type of construction is seen in Repke, U.S. Pat. No. 4,430,086. While this approach has been effective, it is relatively expensive because of the additional elastic required. It also considerably complicates manufacture of the product. For this reason, disposable diaper designers have turned to the use of heat shrunk elastomers which can be used in the form of relatively wider ribbons to increase bearing area.

Heat shrinkable materials became of interest to diaper designers as another method for overcoming the cutting and chafing problem caused by narrow elastic. A considerable number of patents have issued, beginning about 1980, directed to the use of heat shrinkable elastic ribbons placed in marginal areas of disposable diapers. In some of these the heat shrinkable elastomer is used only in the leg area, along the longitudinal margins. In others it is used only in the waist area along the transverse margins of the diaper. In still other constructions, the heat shrinkable elastic is used in both locations. Representative examples of disposable diapers using heat shrunk elastic are found among the following U.S. Pat. Nos.: Repke et al, 4,205,679 and 4,430,086; Mesek et al, 4,324,245 and 4,352,355; Pieniak, 4,333,782; Pieniak et al, 4,337,771 and 4,413,623; Sciaraffa et al, 4,381,781; Sigl, 4,486,192; Kievit et al, 4,515,595; and Relter, 4,563,185. The following British patent applications Nos. are also of interest: Lash, GB 2,136,677A and Chapman et al, GB 2,136,678A.

All of the above patents use discrete ribbons of the heat shrinkable elastic material. These differ greatly in configuration, location, method of attachment, and area in which they are heat shrunk.

The inventors of the above diapers have not discussed suitable equipment for manufacturing them at any length. In making an elastic leg diaper having rubber elastic, an end-to-end assembly is normally held under sufficient tension during manufacturing to prevent wrinkling of the edges. U.S. Pat. Nos. to Buell, 4,081,301; Gore, 4,239,578; Teed, 4,309,236, 4,325,372, and 4,405,397; Frick 4,397,704; and Frick et al, 4,371,417 are exemplary of patents showing equipment for the insertion of elastic along the longitudinal edges of disposable diapers. Sigl, U.S. Pat. No. 4,412,881 and Sabee, U.S. Pat. No. 4,227,952 show equipment for insertion of discrete lengths of tensioned elastic along longitudinal edges. In addition, these following U.S. Pat. Nos. show methods and apparatus for inserting elastic inserts transversely across the ends of diapers forming the waist portions: Kiela, 3,844,288; Rega, 4,240,866; Joa, 4,284,454; and Pieniak, 4,488,923. Klasek, in U.S. Pat. No. 4,293,367 shows a method and apparatus for contouring elastic around longitudinal leg cutouts of disposable diapers. This list is cited as being exemplary only and is not intended to be all inclusive. None of the patents noted above are specifically concerned with the insertion of an untensioned heat shrinkable polymer ribbon and its subsequent heat treatment.

SUMMARY OF THE INVENTION

The present invention concerns a method and apparatus for the manufacture of diapers having elastic leg and/or waist areas formed using areas of heat shrinkable elastomeric materials located in the appropriate marginal zones of the diaper. These heat shrinkable elastomeric materials are those which are heat unstable and relatively inelastic in their unshrunk form and stable and relatively elastic in their heat shrunk for. They may comprise discrete strips located along the appropriate marginal areas of the diapers. Alternatively and preferably, the entire moisture impermeable backing sheet of the diaper comprises the heat shrinkable elastomeric material.

The invention is also considered to include disposable diapers having marginal elastic leg and/or waist areas made using the heat shrinkable elastomeric material as the entire moisture impermeable backing sheet of the diaper unit.

The method includes uniting the individual diaper components to form a continuous end-to-end or side-by-side assembly of diaper units, the end-to-end relationship being preferred. The area adjacent adjoining diaper units preferably forms the waist encircling areas of the diapers. These assemblies are maintained under sufficient longitudinal tension to prevent wrinkling during the manufacturing process. At some point an appropriate area of the longitudinal edges of each diaper unit is heated to a temperature sufficiently high to enable shrinkage of the elastomeric material. Immediately thereafter the marginal longitudinal tension is relaxed while tension is maintained in the central portion of the assembly. The marginal tension is kept in relaxed condition for a sufficient time for the heated elastomeric material to shrink and cool to a temperature where it is again stable, thereby creating marginal elasticized zones on the diapers.

A major element of novelty of the present invention is the provision for maintaining tension along the central portion of the assembly of diaper units while relaxing the tension along the margins to permit essentially free shrinkage of the heated portions. This is accomplished by running the assembly after marginal heating over a series of rolls which are cylindrical in the central portion but tapered at each end. The heated edges of the diaper overhang the tapered portions. In this manner, as the edges shrink the circumferential distance they travel over the tapered ends of the rolls is significantly less than the circumferential distance traveled by the central portion of the diaper assembly. A sufficient number of rolls are employed to permit the desired marginal shrinkage to occur and to further allow the heated areas to cool to the point that they are again stable. At some point beyond this, when the heat treated and now elastic marginal portions have again become stable, they can once more be stretched, if desired, as the assembly moves further through the diaper making machinery. The diapers may also or alternatively be heated transversely to produce elasticized areas. This is preferably done by heating the appropriate localized areas with a hot roll or other means. Preferably, simultaneously with the heating or immediately thereafter, individual diapers are severed from the diaper units to release any transverse tension that might be present. This permits the heat treated end portions of the diaper units to shrink freely until they have sufficiently cooled to become heat stable and elastic. Alternatively, the diaper assembly is allowed to remain intact during transverse shrinkage and the transverse tension is relaxed by some other means, such as festooning the assembly between two roll pairs.

The equipment and method just described can be used with marginal ribbons of the heat shrinkable elastic material which are inserted into appropriate locations during diaper assembly. However, in order to simplify construction, it is preferable to make the entire backing sheet of the heat shrinkable polymeric material. Only those marginal zones which are to be elasticized are heated and allowed to shrink as previously described.

It is an object of the present invention to provide a method and apparatus for the manufacture of disposable diapers or similar products having marginal elasticized areas.

It is also an object to provide a method and apparatus for making disposable diapers having elasticized marginal areas using a heat shrinkable polymeric material which is elastic after being heat shrunk.

It is a further object to provide a method and apparatus in which the longitudinal marginal areas are heat shrunk by relaxing the tension thereon while maintaining tension on the central portion of an end-to-end assembly of diaper units.

It is still a further object to provide diaper manufacturing machinery having double end tapered rolls to permit heat shrinking of marginally heated areas.

It is yet another object to provide a new disposable diaper or similar product having marginal elasticized zones in which the entire backing sheet is made of a heat shrinkable polymeric material.

These and many other objects will become readily apparent to those skilled in the art upon reading the following detailed description taken in conjunction with the drawings.

BRIEF DESCRIPTION OF THE DRAWINGS

FIGS. 11 and 12 are right side views of two embodiments of a transverse edge heat shrinking station of the equipment.

DESCRIPTION OF THE PREFERRED EMBODIMENTS

In the description that follows, it will be understood by those skilled in the art that certain terms are relative. Most disposable diapers and adult incontinent pads are assembled in a continuous end-to-end fashion. In this case the sides of the diaper, which wrap around the upper thighs of the wearer, are the longitudinal direction. However, it is known for diapers to be manufactured in a continuous side-to-side assembly as, for example, is shown in Joa, U.S. Pat. No. 4,284,454. In this case, the ends, or waist encircling portion of the diaper is in the longitudinal direction of motion during manufacture. Thus, the terms "longitudinal" and "transverse" are relative and as used herein should not be considered as limiting to one orientation or the other.

Figure 1:
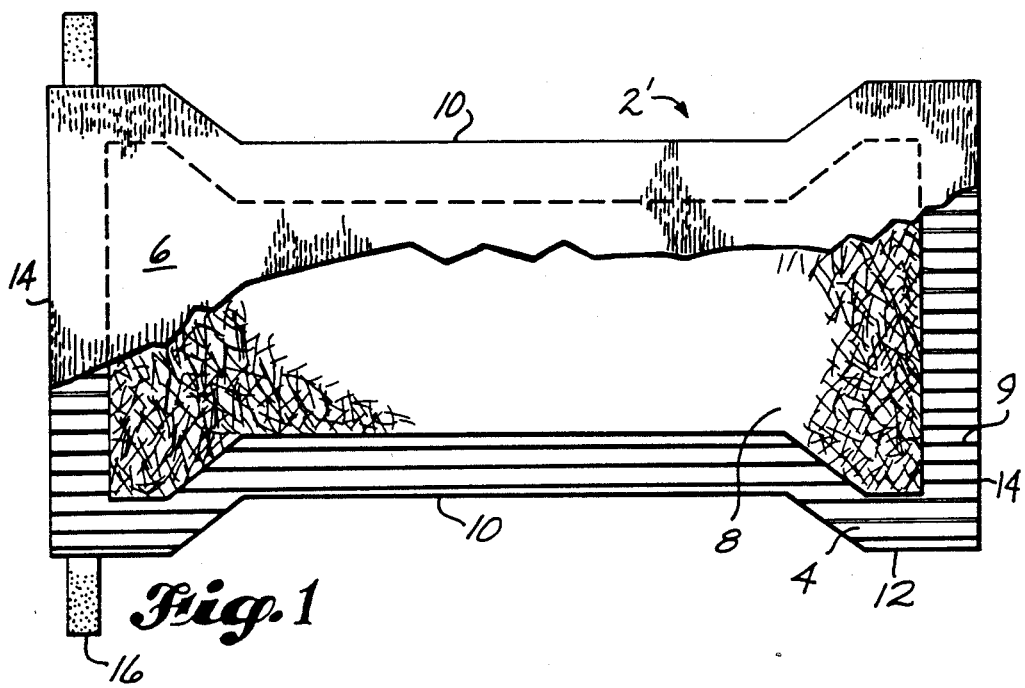
FIGS. 1, 3 and 5 show various embodiments in plan view of disposable diapers of the present invention prior to heat shrinkage of the elastic areas.

The various embodiments of the present invention can most readily be understood by reference to the figures. FIG. 1 shows a diaper 2' whose components have been fully assembled but which is as yet in an unfinished state of manufacture. This is the form of a diaper unit as they are most commonly found while under light tension in an end-to-end assembly on a diaper making machine. It comprises a moisture impervious backsheet 4 which, in the present case, is a biaxially oriented heat shrinkable thermoplastic material. This backing film is shown here in its relative inelastic heat unstable, unshrunk state. When heat shrunk, it becomes elastic having an extensibility of up to 100%, or even greater. Backing sheet 4 is overlaid by a moisture absorbent fluff filler pad 8. This, in turn, is covered with a moisture pervious nonwoven top sheet 6. The entire assembly is bonded together by a plurality of fine hot melt adhesive lines 9. Each diaper unit has longitudinal margins 10 which define the leg encircling crotch areas and longitudinal margins 12 which are located in waistband area. The diapers further have transverse margins 14 which further define the ends of the waistband areas. Adhesive attachment tapes 16 complete the unit.

Figure 2:
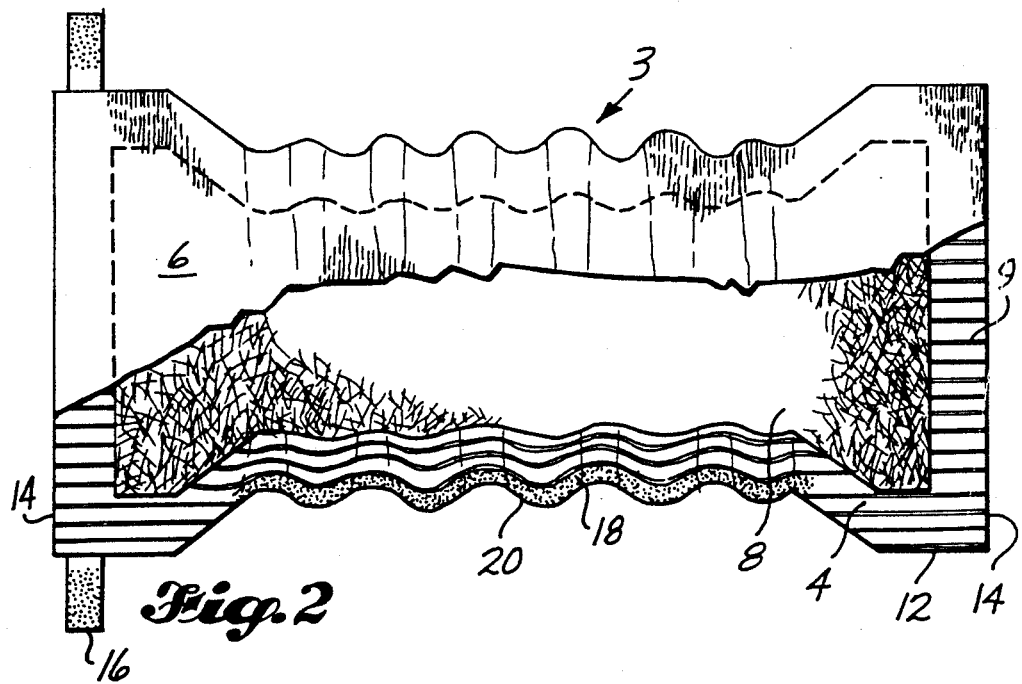
FIGS. 2, 4, 6 and 7 show similar embodiments after the elastic areas have been heat shrunk.

FIG. 2 shows the diaper of FIG. 1 in which the longitudinal margins 10 have been heat shrunk in the leg encircling areas to form elastic portions. These ensure a tight fit and are important in preventing leakage when worn by an infant or adult user. The diaper of FIG. 2 is shown without any longitudinal or transverse restraint. As a result, the heat shrunk marginal areas 18 will tend to form a shirred or wrinkled edge 20 with accompanying transverse folds. When placed on a wearer the shirred edge 20 is generally placed under tension and the diaper surface is again drawn reasonably flat.

The temperature to which the longitudinal edge of a diaper of the type shown in FIGS. 1 and 2 must be heated is dependent upon the particular polymeric material which is used. These temperatures will generally range between about 80°–120° C. The amount of shrinkage obtained is somewhat dependent upon the temperature to which the polymeric material is heated and the manner in which it is allowed to relax while being cooled. These points will be discussed later in considerable detail.

Figure 3:
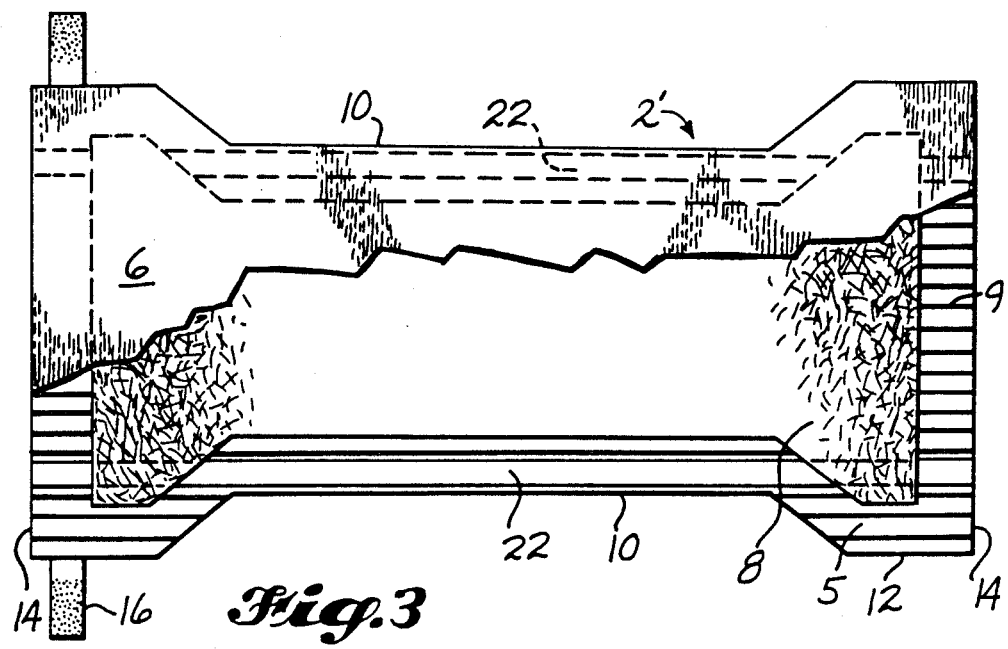
Figure 4:
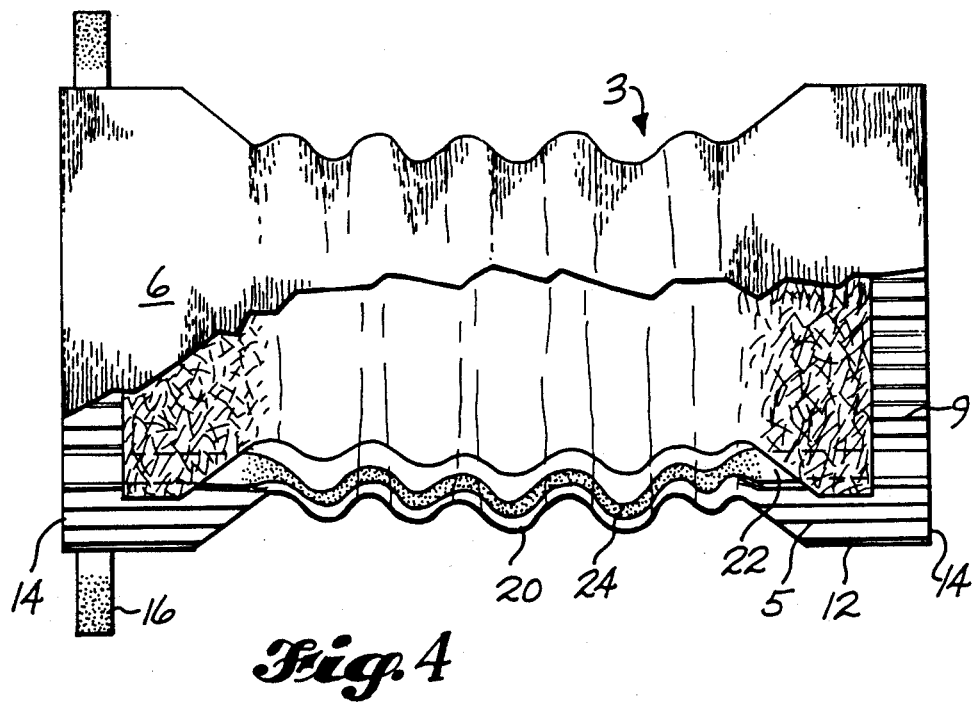

An alternative manner of making a similar elastic leg diaper to that shown in FIGS. 1 and 2 is seen in FIGS. 3 and 4. It might be noted here that in all of the figures, like numbers indicate like components. The diapers shown in FIGS. 3 and 4 are of a more conventional construction similar to that in which rubber elastic is used in the leg encircling areas. Here the backing film is of a more conventional material 5 which would typically be pigmented polyethylene film having a thickness in the range of 0.02–0.04 mm. In the present case, longitudinal ribbons 22 of the heat shrinkable polymeric material are placed along each longitudinal edge of the diaper. These would generally be of a width in the range of about 10–15 mm and may run the full length of the diaper, as shown in FIG. 3. Alternatively, they may be discrete lengths of material located only in the crotch encircling area parallel to longitudinal edge 10. FIG. 4 shows the diaper assembly of the diaper unit of FIG. 3 after the polymeric tape has been heat shrunk along the marginal area 10. This results in a longitudinal and transverse shrinkage to the range of 50–80% of original dimensions in the heated area to produce an elastic area 24. The end portions of tape 22 located in the waist areas of the diaper remain in the original unshrunk form.

Figure 5:
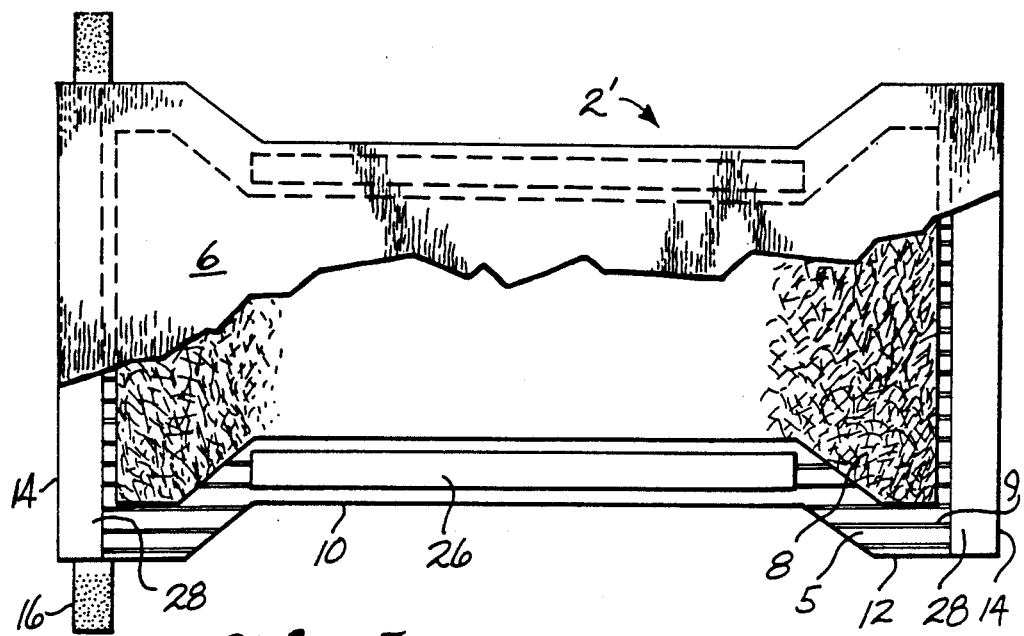
Figure 6:
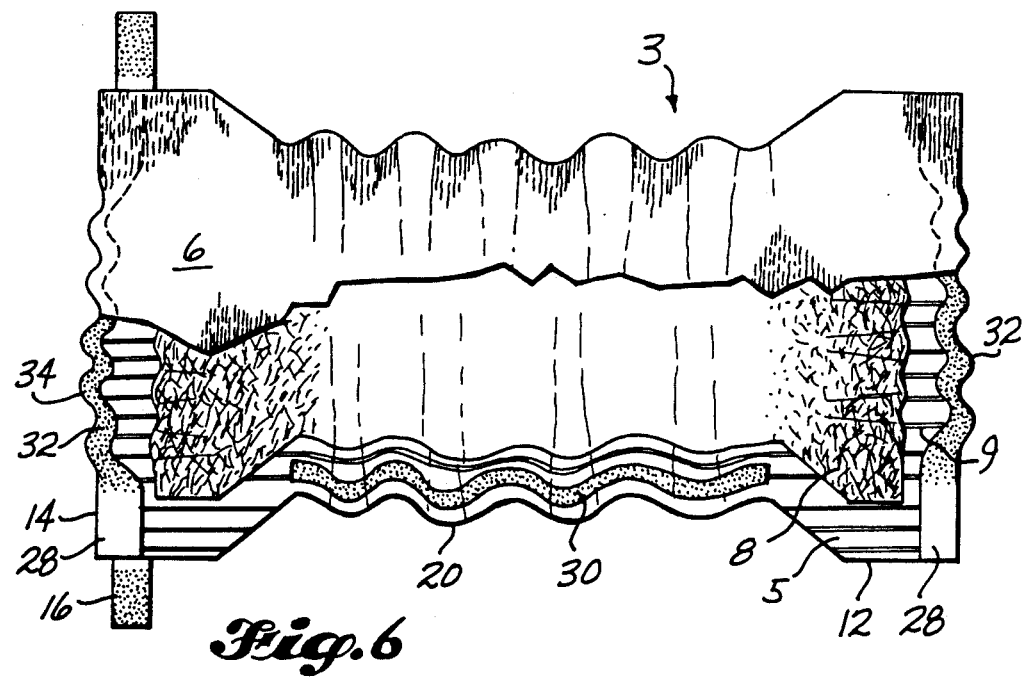

FIGS. 5 and 6 show yet another version of a diaper employing heat shrinkable polymeric material to create elasticized areas along both the leg and waist encircling portions of the diaper. Again, as shown in FIGS. 3 and 4, the backing sheet is a conventional material such as pigmented polyethylene. In the present construction discrete lengths of heat shrinkable polymeric material 26 are placed in each leg encircling area of the diaper. Similarly, transverse heat shrinkable ribbons 28 are laid across each waist area of the diaper. Machinery to lay up a diaper of the type shown in FIG. 5 is conventional to this point. As one example, the longitudinal polymeric ribbons 26 may be placed in the assembly by any of the assembly machines previously noted that are designed to lay in discrete lengths of elastic. However, here the ribbons 26 are not stretched when put in place. The transverse ribbons 28 could conveniently be placed by machinery such as that described by Frick in U.S. Pat. No. 3,758,363. FIG. 6 shows the diaper unit of FIG. 5 after the polymeric ribbons have been shrunk to produce longitudinal elastic zones 30 and transverse elastic zones 32. As shown in the previous examples, this results in a shirred longitudinal edge 20 and, additionally, a shirred transverse edge 34. This construction helps to ensure a tight, leak-proof fit in both the leg and waist areas.

Figure 7:
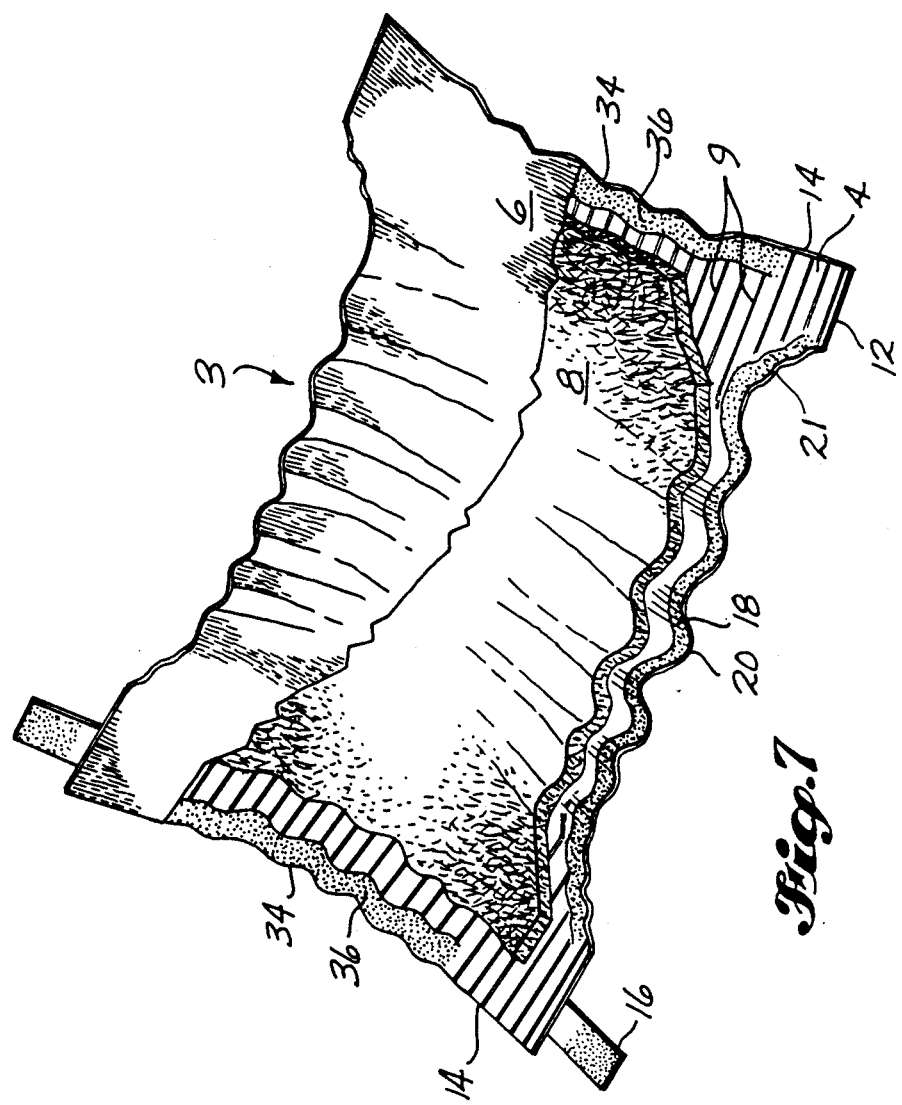

FIG. 7 shows a diaper of similar construction to that shown in FIGS. 1 and 2 in which the entire backing film is the heat shrinkable thermoplastic polymeric material. Here again, both the leg and waist encircling areas have been heat shrunk to produce elastic zones 18 and 36, respectively. The present method has an additional important advantage shown in FIG. 7. It is a very simple matter to elasticize the entire leg cutout area so that the transition zones 21 are also elastic. This ensures a tighter fit around the entire thigh area of the wearer.

There are major advantages to the manufacturer in producing diapers having the configuration of those shown in FIGS. 1, 2, and 7. Manufacturing equipment is much simpler since no provision need be made for inserting either longitudinal or transverse elastic. The backing film itself serves this purpose. However, one further complication is present which had not been adequately solved until the present time, especially in the case of heat shrinking in the longitudinal or machine direction. As noted earlier, after the heat shrinkable material has been heated to a sufficient temperature at which shrinkage can occur, any restraining tension which would tend to prevent such shrinkage must be removed. Diapers are normally manufactured under some longitudinal tension in order to prevent wrinkling during manufacture. This tension is also necessary to ensure that the timing built into various machine components does not fall out of synchronization resulting in misassembled diaper components. The application of longitudinal tension also unavoidably causes a lesser amount of transverse tension on the diaper assembly. Thus, in order to effectively use the heat shrinkable elastomeric materials, conflicting demands must be met. Somehow tension must be maintained on the end-to-end diaper assembly to meet the machine demands, yet the tension must be relaxed at least for a sufficient time to enable shrinkage to occur in any heated areas. The present design of a diaper manufacturing machine has successfully accommodated these conflicting requirements as they apply to both longitudinal and transverse heat shrinkage.

Figure 8:
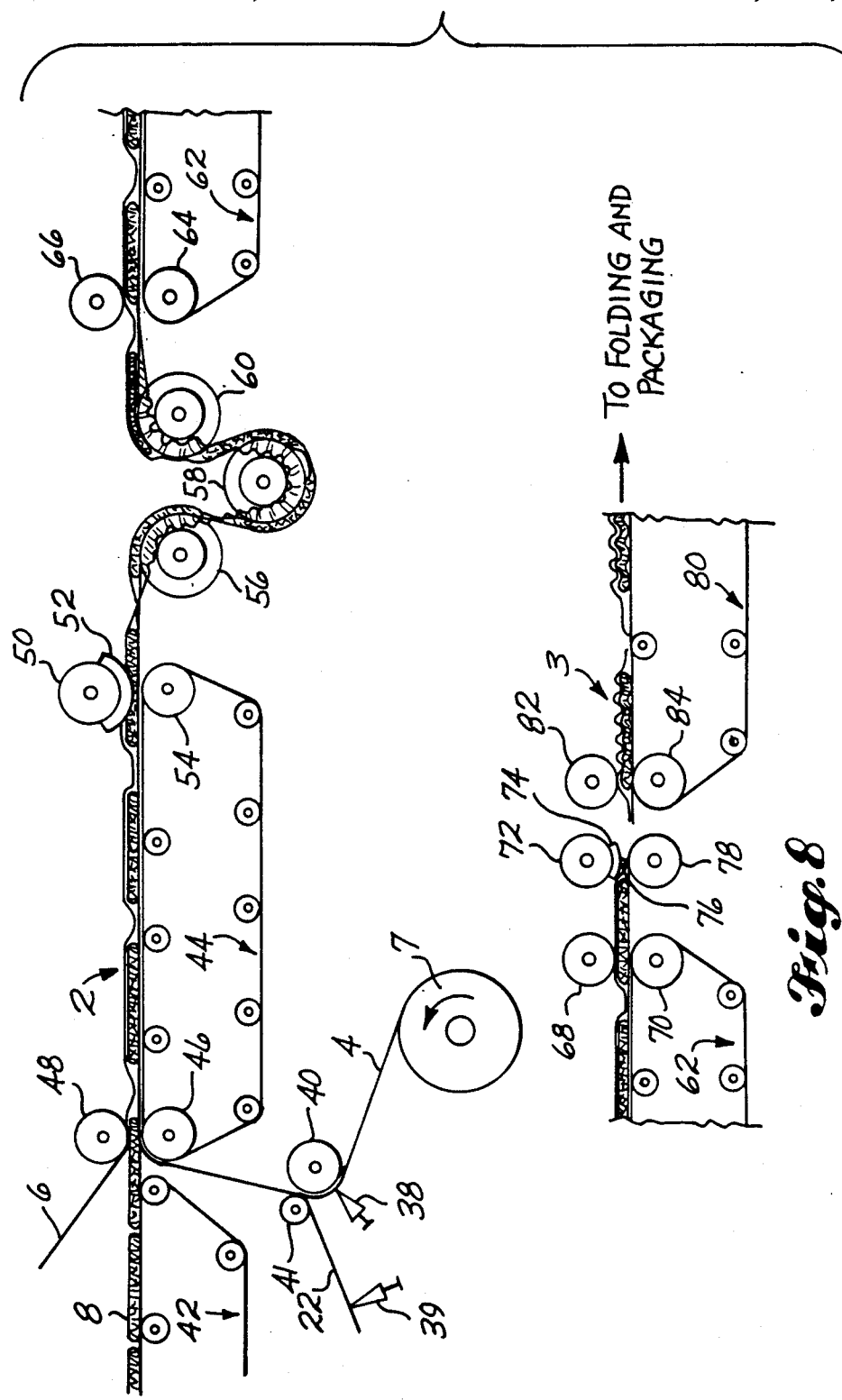
FIG. 8 shows a representation in right side elevation of manufacturing equipment for the disposable diapers of the present invention.

Machinery suitable for manufacture of diapers similar to those just discussed is shown in FIGS. 8 through 12, with FIG. 8 being an overall view. Here the moisture impervious backing sheet 4 is withdrawn from a supply roll 7 by feed rolls 40, 41. The fine line pattern of hot melt adhesive 9 may be applied to the backing sheet by an applicator 38. If the backing film is not a heat shrinkable material in its own right, marginally located longitudinal ribbons 22 of such a material may be applied to the backing sheet between rolls 40 and 41. A flexible adhesive applied by applicator 39 may alternatively be used to create a greater bonding area between marginal ribbons 22 and backing sheet 4 than would otherwise be provided by the adhesive fine lines 9. As another alternative, the heat shrinkable film 22 could be bonded by heat sealing, using a temperature below that at which significant shrinkage occurs. Other bonding techniques such as ultrasonic welding may be also be employed when separate ribbons of the heat shrinkable material are used in the diaper construction. The heat shrinkable ribbon 22 may also be applied to the cover sheet 6 if desired.

The backing material 4, which may now have marginal ribbons 22 attached, enters a diaper component assembly conveyor 44 between pressure rolls 46 and 48. At this point the moisture pervious top sheet 6 and the moisture absorbent pads 8 are combined with the backing sheet. Pads 8 have been preformed and severed into units as they advance on conveyor 42. The end-to-end assembly of diaper units 2 moves along conveyor 44 until it encounters opposing rolls 50 and 54. Roll 50 has a pair of heated shoes 52 mounted so as to engage each longitudinal edge of the diaper units in the leg encircling areas. These hot shoes will heat the heat shrinkable thermoplastic film to a temperature which will normally be at least 80° C.

As an alternative to the construction shown, roll 50 with hot shoe 52 and backup roll 54 could be reversed so that the heat is applied directly to the backing film.

Figure 9:
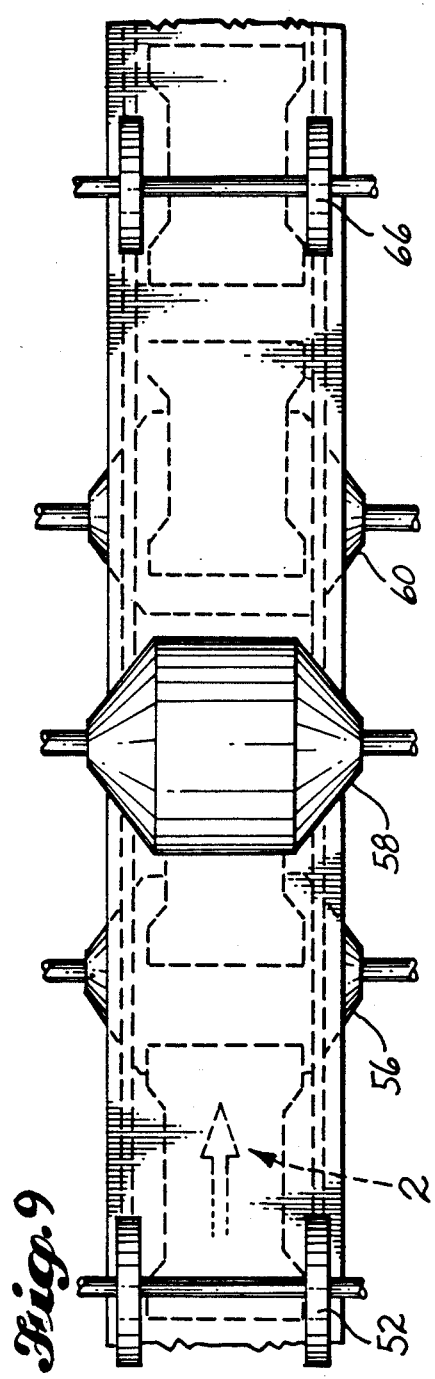
FIGS. 9 and 10 are more detailed top plan and right side views, respectively, of the longitudinal edge heat shrinking station of the equipment.
Figure 10:
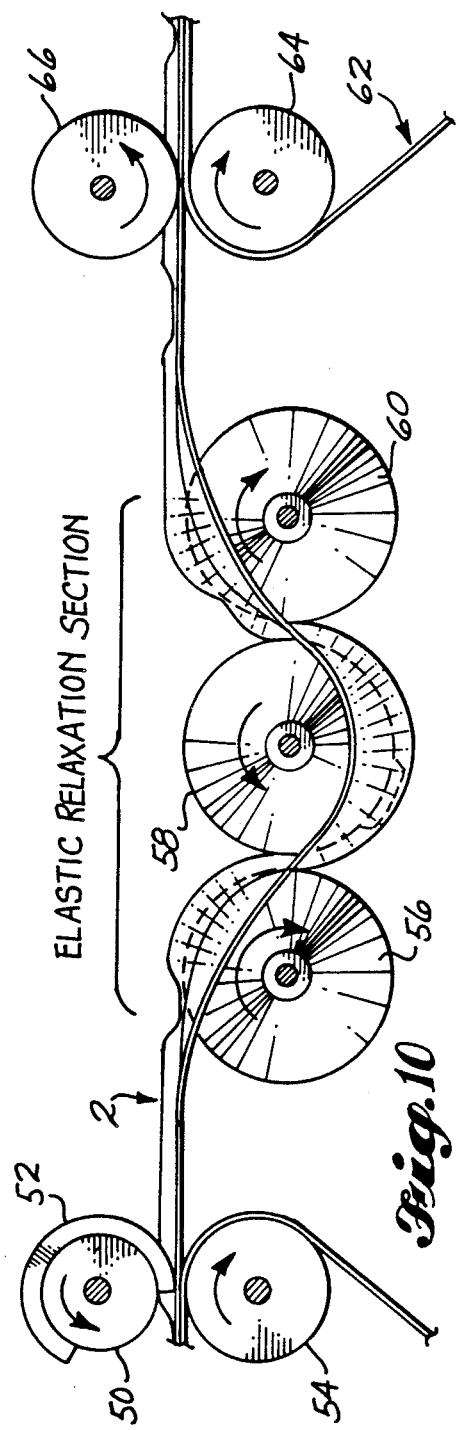

Immediately after leaving the heating area on conveyor 44, the diaper assembly passes over a plurality of rolls where longitudinal margin shrinkage occurs. Normally at least three such rolls 56, 58, 60 are employed and more may be used if additional time is required for shrinkage and cooling until a heat stable state is again attained. Rolls 56, 58, and 60 are generally cylindrical in their central section but tapered at each end. This construction is best seen in FIG. 9. While passing over the rolls, normal tension is maintained in the central or pad area of the diaper assembly. However, the now heated longitudinal marginal areas, which overhang over the tapered portion of the rolls, are free to shrink to the point at which the tapered portion of the roll is encountered. If shrinkage to 50% of the original longitudinal dimension is desired in the leg encircling areas, the circumference of the tapered portion at which the marginal area will ultimately be restrained should be half that of the circumference of the central portion of the rolls. The use of these double tapered rolls is at the heart of the present method and apparatus. It is these rolls that enable the conflicting demands for maintenance of longitudinal tension and relaxation of marginal tension to be met.

After the marginal areas of the end-to-end diaper assembly have been shrunk and are again heat stable, they pass from the double tapered rolls onto an additional conveyor 62 between rolls 64, 66 which serve to maintain tension on the units. Rolls 68, 70 at the discharge end of conveyor 62 serve a similar purpose.

If the diaper waist areas are also to be elasticized, they may at this point pass between rolls 72, 78. Roll 72 has a hot shoe 74 which is timed to engage and heat the end or transverse margins of the diaper units. This roll may also have a severing knife 76, in which case roll 78 serves as an anvil roll. Alternatively, the severing knife may be on a separate roll 77 located immediately after the roll pair 70, 72 (FIG. 12). The now severed individual diapers 3 pass onto another conveyor 80 between rolls 82, 84. Conveyor 80 moves at a somewhat faster speed than conveyor 62 so that the diapers are separated by a small interval. All restraining forces on diapers 3 are released while they are traveling on conveyor 80. At this point the end margins are free to contract and cool to their stable elastic condition. The diapers move from conveyor 80 to conventional machinery, not shown, where they are folded and packaged.

The preferred form of the present invention utilizes the heat shrinkable thermoplastic film as the entire backing film for the diaper and does not utilize longitudinal or transverse heat shrinkable inserts such as are employed in the embodiments shown in FIGS. 5 and 6. However, where it is desired to use transverse inserts 28, these may be applied at any convenient location prior to assembly of the individual components on conveyor 44. As noted earlier, apparatus for performing this step is conventional. Conveniently the transverse inserts might be applied to backing film 40 at some point between feed rolls 40, 41 and assembly rolls 46, 48 on conveyor 44. Many other such variations will be apparent to those who are skilled in the art.

EXAMPLE

The various components used in the manufacture of infant diapers or adult incontinent pads are well known within the industry. The moisture permeable top or body contacting sheet has a basis weight usually in the range of 18–26 g/m$^2$ and may typically be a carded polyester fiber with a latex binder or spun bonded polypropylene having continuous fibers of 2–5 denier thermally bonded by patterned calendar rolls. Respective examples of these types would be Scott 6822, available from Scott Paper Company, Nonwovens Division, Philadelphia, Pa. or Celestra, available from Crown Zellerbach Corporation, Washougal, Wash. The moisture impermeable diaper backing sheet may be a low density polyethylene film having a thickness in the range of 0.02–0.04 mm (0.75–1.5 mils). This material is frequently microembossed to better retain attachment tapes. An example of such a conventional backing material would be Clopay Code 53, available from Clopay Corporation, Cincinnati, Ohio.

The preferred backing film is a biaxially oriented heat shrinkable elastomeric material of the type that is heat unstable and relatively inelastic in its unshrunk form and stable and relatively elastic in its heat shrunk form. This may be used either for the entire backing sheet or for ribbon-like inserts along the marginal portions of the backing sheet. One such material is Cryovac SDX-0820, available for Cyrovac Division, W. R. Grace Company, Duncan, S.C. This material is a biaxially oriented irradiated polyethylene that becomes heat shrinkable at temperatures generally falling within the range between 80°–95° C. Unrestrained shrinkage after heating this material to the above temperature range will generally be to about 50% of original dimensions. Lower shrinkage can be achieved in one of several ways. Control of the amount of stretch during film formation is one suitable way. As one example, if it is only desired to produce elasticized leg opening areas on a diaper, a uniaxially oriented film would normally be quite suitable. Control of temperature to which the film is heated, and the subsequent rate of cooling, is another way in which shrinkage can be controlled.

Flexible rapid setting hot melt adhesives, which may be used to bind separate heat shrinkable ribbons and may also be used as the fine line adhesives for uniting the entire assembly, are commonly formulated from ethylene-vinyl acetate resins used with tackifiers and other additives. These adhesives tend to be somewhat tacky and flexible at room temperature. One suitable material is available from H. B. Fuller Company, Vadnais Heights, Minn. as Type HL 1048N.

Large sized infant diapers were made using the above Cryovac material in place of the more conventional polyethylene as the moisture impervious backing film. These diapers were 495 mm long and 337 mm wide and weighed a total of 72 g. The pad was fluffed bleached kraft softwood pulp having a density in the range of 0.07–0.08 g/cm$^3$. The backing film had a thickness of 0.015 mm. It is possible to use a film this thin because its tensile strength is approximately twice that of the normal low density polyethylene film used for the backing material. The diapers were conventionally assembled. After this the longitudinal margins were heated to a temperture of approximately 95° C. over a width of about 10 mm and allowed to shrink. Subsequently, the transverse waist areas of the diapers were heated to a slightly lower temperature over a width of about 15 mm and allowed to shrink freely. The ultimate diaper had an extensibility in the leg area of approximately 100% with about 40% extensibility in the waist areas.

It will be readily apparent to those skilled in the art that many variations could be made without departing from the spirit of the present invention. Thus, the invention is to be considered as being limited only by the following claims.

We claim:

1. A method of making a disposable diaper of the type having a moisture permeable skin contacting cover sheet, a moisture impermeable backing sheet, and a moisture absorbing filler pad disposed therebetween which comprises:
    uniting the individual diaper components to form a continuous end-to-end or side-by-side assembly of diaper units;
    providing areas of heat shrinkable elastomeric material at least along one longitudinal edge of the diaper assembly, said elastomeric material being of the type that is heat unstable and relatively inelastic in its unshrunk form and stable and relatively elastic in its heat shrunk form;
    maintaining sufficient longitudinal tension on the diaper unit assembly to prevent wrinkling thereof;
    heating the longitudinal edges of each diaper unit in the assembly in the areas of the heat shrinkable elastomeric material to a temperature sufficient to enable shrinkage of said elastomeric material;
    immediately thereafter relaxing the longitudinal edge tension of the heated diaper units while maintaining said tension in the central portion of the diaper units for a time sufficient to permit the heated elastomeric material to shrink and cool to a temperature where said elastomeric material is stable, thereby creating marginal elasticized zones on said diapers.

2. The method of claim 1 wherein said relaxing includes passing the assembly of diaper units over a series of transversely oriented rolls immediately following said edge heating, the rolls being essentially cylindrical in their central portion but tapered at each end so that the longitudinal edges of the diaper assembly overhang the tapered ends, whereby the distance traveled by said longitudinal edges of the diaper unit assembly are sufficiently less than the distance traveled by the central portion of diaper units so as to relax the longitudinal marginal tension.

3. The method of claim 2 which includes providing at least three end tapered rolls.

4. The method of claim 1 wherein said providing step includes a separate strip of heat shrinkable elastomeric material is placed along each longitudinal edge of the diaper units.

5. The method of claim 1 in which the entire diaper backing sheet comprises heat shrinkable elastomeric material.

6. The method of claim 1 in which the diaper units in the assembly are in an end-to-end relationship so that the longitudinal edges of the diaper units correspond to the leg encircling portions and the area adjacent adjoining diaper units forms waist encircling portions of the diapers.

7. The method of claim 6 in which said waist encircling areas of the diapers are essentially devoid of filler pad and which further includes providing areas of heat shrinkable elastomeric material in at least one of said waist encircling areas of each diaper unit, heating said heat shrinkable material in the waist areas following shrinkage of the elastomeric material in the longitudinal edge zones, and relaxing any transverse tension present to permit the heated elastomeric material to shrink and cool to a temperature where said elastomeric material is stable thereby creating elasticized waist areas in the diapers.

8. The method of claim 7 wherein said transverse relaxing includes simultaneously with said heating or immediately thereafter severing the individual diaper units from the continuous assembly.

9. The method of claim 8 wherein a separate strip of heat shrinkable elastomeric material is placed in said waist areas.

10. The method of claim 8 wherein the entire diaper backing sheet comprises heat shrinkable elastomeric material.

11. In a machine for manufacturing disposable diapers by combining a moisture permeable skin contacting cover sheet, a moisture impermeable backing sheet, and a moisture absorbing filler pad disposed therebetween, said diapers further having areas of a heat shrinkable elastomeric material in at least one edge thereof, the improvement which comprises:

means for assembling and combining the cover sheet, backing sheet, filler pad, and heat shrinkable elastomeric material into a continuous end-to-end or side-by-side assembly of diaper units;

means for maintaining longitudinal tension on the diaper unit assembly;

means for heating the longitudinal edges of each diaper unit in the areas of the heat shrinkable elastomeric material to a temperature sufficient to enable shrinkage of said elastomeric material;

roll means positioned immediately following said heating means for relaxing the longitudinal edge tension on the diaper unit assembly while maintaining said tension in the central portion of the diaper units, said roll means comprising a series of transverse rolls that are essentially cylindrical in the central portion but tapered at each end, so that the diaper edges overhang the tapered portions and the distance traveled by the marginal portions of the assembly when passing over the roll means is less than the distance traveled by the central portion of the diaper units, whereby the heated areas are enabled to shrink unrestrained and cool to a stable heat shrunk state in order to create marginal elasticized zones on the diapers.

12. The apparatus of claim 11 in which the roll means includes at least three end tapered rolls.

13. The apparatus of claim 11 in which the diaper component assembling means forms an end-to-end assembly of diaper units so that the area adjacent adjoining diaper units contains the waist encircling portions of the diapers.

14. The apparatus of claim 13 which further includes transverse heating means for heating the heat shrinkable elastomeric material in at least one of said waist encircling areas of each diaper unit to a temperature sufficient to enable shrinkage of said elastomeric material, said transverse heating means being located sufficiently downstream so as to sequentially follow the heating, shrinkage and cooling of the elastomeric material along the longitudinal edges, and means following said heating means to relax any transverse tension on the diaper assembly so that the heated transverse elastomeric material is allowed to shrink and cool while unrestrained.

15. The apparatus of claim 14 wherein said transverse relaxing means includes transverse severing means located adjacent to said transverse heating means to sever the individual diaper units from the continuous assembly simultaneously with or immediately thereafter exposure to said transverse heating means.

16. The apparatus of claim 15 which includes transverse heating means to heat both waist encircling areas of each diaper unit.

* * * * *